(12) United States Patent
Marion et al.

(10) Patent No.: US 7,851,477 B2
(45) Date of Patent: Dec. 14, 2010

(54) METHOD FOR THE TREATMENT OF SKIN

(75) Inventors: Catherine Marion, Antony (FR); Gabrielle Sore, Paris (FR)

(73) Assignee: L'Oreal, Paris (FR)

( * ) Notice: Subject to any disclaimer, the term of this patent is extended or adjusted under 35 U.S.C. 154(b) by 1594 days.

(21) Appl. No.: 10/843,463

(22) Filed: May 12, 2004

(65) Prior Publication Data

US 2005/0004146 A1 Jan. 6, 2005

Related U.S. Application Data

(60) Provisional application No. 60/474,674, filed on Jun. 2, 2003.

(30) Foreign Application Priority Data

May 22, 2003 (FR) .................................. 03 06159

(51) Int. Cl.
*A61K 31/522* (2006.01)
*A61K 31/455* (2006.01)
*A61K 31/7048* (2006.01)
*A61K 31/375* (2006.01)
*A61K 31/355* (2006.01)

(52) U.S. Cl. .................... 514/263.31; 514/27; 514/356; 514/458; 514/474

(58) Field of Classification Search ............ 514/263.31, 514/27, 356, 458, 474
See application file for complete search history.

(56) References Cited

U.S. PATENT DOCUMENTS

| 4,945,094 | A | | 7/1990 | Salim |
| 5,523,090 | A | | 6/1996 | Znaiden et al. |
| 6,136,806 | A | * | 10/2000 | Hittel .................. 514/294 |
| 6,680,062 | B2 | * | 1/2004 | Muizzuddin et al. ........ 424/401 |

FOREIGN PATENT DOCUMENTS

| CA | 944695 | | 4/1974 |
| EP | 0 728 472 | | 8/1996 |
| FR | 2035798 | | 12/1970 |
| FR | 2 831 440 | | 5/2003 |
| JP | 08-253405 | | 10/1996 |
| JP | 10-511360 | | 11/1998 |
| JP | 2002-544218 | | 12/2002 |
| WO | WO 96/19228 | | 6/1996 |
| WO | WO 99/47141 A1 | * | 9/1999 |
| WO | WO 00/69408 | | 11/2000 |
| WO | WO 03/039418 | | 5/2003 |

OTHER PUBLICATIONS

Dorland's Illustrated Medical Dictionary, 28$^{th}$ Edition, 1994 p. 576.*
Shinobu et al. JP200186069A (Apr. 2000) transulation.pp. 1-20.*
G. Stuettgen, et al., "Dopamine Effects on the Microcirculation and Veins of the Skin After Local Application and Their Changes by Antagonistic Drugs", Archives of Dermatological Research, 266, 1979, pp. 59-73.
Patent Abstracts of Japan, JP 2000-186036, Jul. 4, 2000.
P.U. Giacomoni, et al., "Anti-Erythemal Properties of a Natural Extract: Efficacy and Possible Mechanisms of Action," Seifen-Öele-Fette-Wachse Journal, 2000, vol. 126, No. ½, pp. 14-17.
Hicks, M.B., et al. "Tea Preparation and its Influence on Methylxanthine Concentration" Dept. of Nutrition and Food Science, Auburn University, Auburn, AL 36849, USA, Food Research International, vol. 29, Issue 3-4, Apr. 1996, (pp. 325-330), abstract.
Kakuda T, et al. "Inhibiting Effects of Theanine on Caffeine Stimulation Evaluated by EEG in the Rat" Science Links Japan, Journal Title; Biosci Biotechnol Biochem, Journal Code:G0021A, Issn:0916-8451, vol. 64;No. 2 (pp. 287-293), Publish Country Japan, http://sciencelinks. jp, abstract, 2000.

* cited by examiner

*Primary Examiner*—Jennifer M Kim
(74) *Attorney, Agent, or Firm*—Oblon, Spivak, McClelland, Maier & Neustadt, L.L.P.

(57) ABSTRACT

The present invention relates to a method for the treatment of skin redness by topically applying a composition containing caffeine to the affected skin. The invention method finds particular use on persons having at least one of the following symptoms: rosacea, folliculitis or skin irritated by chemical or physical peelings.

16 Claims, No Drawings

METHOD FOR THE TREATMENT OF SKIN

REFERENCE TO PRIOR APPLICATIONS

This application claims priority to U.S. provisional application Ser. No. 60/474,674 filed Jun. 2, 2003, and to French patent application 0306159 filed May 22, 2003, both incorporated herein by reference.

FIELD OF THE INVENTION

The present invention relates to a method for the treatment of skin, especially skin redness, including, for example, a treatment of red blotches located on the skin, comprising the topical application to at least the affected areas of the skin of a composition comprising caffeine and a physiologically acceptable medium. The invention method finds particular use for persons having at least one of the following symptoms: rosacea, folliculitis or skin irritated by chemical or physical peelings.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Rosacea is a chronic benign dermatosis which affects mainly the face of subjects with fine and light skin, between 30 and 60 years of age, more particularly women. It is characterized by a persistent facial erythema, frequent flushes and telangiectasia. Although papules and pustules can intermittently occur, rosacea should not be confused with acne, since the comedones and cysts which characterize acne are not symptoms of rosacea.

Four stages are distinguishable in the progression of rosacea:
- the stage of vasomotor flushes of the face and of the neck and shoulders, caused by changes in temperature, physical effort, emotions, solar exposure or during the ingestion of certain foods or drinks. This phenomenon is due to a delay in the emptying of the venous plexus;
- the stage of acne rosacea or erythro-acne rosacea which corresponds to a permanent erythematous state of the face associated with telangiectasia. The erythrosis has a variable colour which may range from light pink to intense red or even purplish. This stage can sometimes be accompanied by a permanent hard oedema;
- the inflammatory stage with the episode of inflammatory pustules and papules on an erythemato-telangiectatic base; phase of a state characteristic of rosacea; and
- the stage of rhinophyma which is essentially masculine and manifests itself by constant swelling of certain areas of the face. The facies is rubicund and the nose is red and large, covered in bumps, associated with sebaceous hyperplasia and fibrous reorganization of the connective tissue.

Various effective treatments have been proposed, which not only can slow the progression of rosacea, but also cure the symptoms described above. They may be cosmetic, dermatological or physical treatments.

Thus, it is known to use anti-acne rosacea products, having a vasculotropic effect, for treating mild to moderate acne rosacea characteristic of the first two stages of rosacea. At the third stage, the inflammatory lesions can be treated with an antibiotic gel or cream based on metronidazole or azelaic acid, for example. In the case of a more severe condition, oral antibiotic therapy may be combined with the topical treatment. The use of tetracyclines is recommended at this stage. At the fourth stage of rosacea, only the use of physical methods such as laser is possible because no medicament is effective.

Now, these treatments, and in particular the cosmetic products topically applied to skin with acne rosacea, have the disadvantage of being relatively irritating and therefore poorly tolerated by subjects who generally have a very sensitive skin. The least irritating treatments are moreover the least effective.

It is therefore possible to understand the importance of acting from the first stages of rosacea in order to avoid its aggravation, by having recourse to nonaggressive cosmetic treatments for the skin which can also be used at the third stage of rosacea, in combination with antibiotic therapy.

SUMMARY OF THE INVENTION

Now, the inventors have discovered, surprisingly and unexpectedly, that caffeine is effective in the treatment of skin, especially skin redness and including, for example, the treatment of red blotches located on the skin. The invention thus relates in part to the topical application to at least the affected areas of the skin of a composition comprising caffeine and a physiologically acceptable medium. In this regard the invention is particularly beneficial in the treatment of rosacea (especially to attenuate erythro-acne rosacea which is an early stage of rosacea), folliculitis and irritated or irritable skin such as skin irritated by chemical or physical peelings.

This discovery is surprising and unexpected because the literature notes an aggravating role of coffee consumption on rosacea (WILKIN J. K., Oral thermal-induced flushing in erythematotelangiectatic rosacea, *Journal of Investigative Dermatology*, January 1981, 76(1): 15-8). In this regard the present invention may support a competing hypothesis according to which this condition may be triggered more by the heat of the drink than by its caffeine content (Diagnosing an inflamed situation (Rosacea analysis), *Chemist & Druggist*, 26 May 2001, p. 26; Restaurant flushing syndrome: make sure you identify its cause, *Dermatology Times*, July 1993, p. 1). While the latter two publications call into question the causative role of caffeine on rosacea, they however do not note an improvement in rosacea during the consumption of caffeine and therefore do not make it possible a fortiori to suggest that caffeine, applied topically to the skin, can have this effect.

U.S. Pat. No. 6,352,698 describes a composition intended for the treatment of sensitive skin, comprising a hypoallergenic complex which may consist of a combination of lactoferrin, drieline, panthenol and green tea extract containing caffeine. It is indicated that this complex has the property of lowering the reactivity threshold of the skin and of decreasing the magnitude of the reactions of intolerance or the immunoallergic reactions. This complex is thought to act by decreasing the synthesis or the expression of neuromediators. The composition containing it could be used to prepare an immunomodulatory drug which can be used in the treatment of rosacea.

However, up until now, the link between immunodeficiency and rosacea has never been demonstrated. In addition, the symptoms of sensitive skin which the complex described in this patent attenuates are not precisely described and it is possible to understand that this complex does not necessarily act on skin blotches but can, as a variant, decrease the pricklings, pain or pruritus conventionally associated with sensitive skin.

Thus, it was not obvious that caffeine, which is one of the minor constituents of extracts of green tea leaves, could have a marked preventive or curative effect on redness such as red skin blotches, and in particular those linked to the early stages of rosacea.

Moreover, the soothing effect of Cola nitida extracts was known from FR-2 831 440. However, caffeine is combined in Cola nuts with other active ingredients which are in particular tannins and theobromine. Consequently, here again, it was not obvious that caffeine could itself have an effect on red skin blotches.

Finally, the antiirritating effects of caffeine were known from WO 03/039418. It was not however specified on which component of the irritation this compound acted.

Now, the inventors have shown that caffeine acts effectively on redness (e.g., from light pink to intense red or even purplish blotches).

One subject of the present invention is therefore a method for the treatment of skin redness, particularly comprising the topical application, to the skin, of a composition comprising caffeine and a physiologically acceptable medium. Application can be to the skin in general—that is, to a section or area of skin containing the redness (e.g., one or more blotches), or to only the redness (e.g., the blotch or blotches themselves only). Where not specified, application to the skin in general is intended. Where the invention method is preventative only, the skin to which the composition is applied is skin known by the user to be subject to redness.

The method according to the invention is prevents and/or attenuates redness of various origins, in particular those associated with the early stages of rosacea. It can, as a variant, be used on skin which is irritable or irritated either by chemical treatments (e.g., chemical peelings), physical treatments (e.g., laser) or medicinal treatments (e.g., retinoic acid, hydroxy acids). It can, as a variant, be useful in the prevention or treatment of redness of inflammatory origin, in particular folliculitis, such as those subsequent to shaving.

The composition according to the invention is therefore advantageously applied to persons having at least one of the following symptoms: rosacea, irritated or irritable skin or folliculitis. It is for example used following chemical or physical peeling.

The composition according to the invention is preferably applied to the face.

The composition according to the invention preferably comprises a physiologically acceptable medium and an effective amount of caffeine to treat or prevent skin redness such as that appearing as the symptoms of rosacea, irritated or irritable skin, or folliculitis, for example a quantity between 0.05% and 3% by weight, preferably between 0.1 and 1% by weight, including of course 0.2, 0.3, 0.4, 0.5, 0.6, 0.7, 0.8, 0.9, 1.2, 1.4, 1.6, 1.8, 2.0, 2.2, 2.4, 2.6, and 2.8% by weight, and all subranges and values therebetween, relative to the total weight of the composition.

The expression physiologically acceptable medium is understood to mean a medium compatible with the skin and possibly the mucous membranes, the nails, the scalp and/or the hair. A physiologically acceptable medium may be a single material or a combination of materials.

The composition according to the invention may be in any form, such as the form in particular of an aqueous solution or a dispersion of the lotion or syrup type, emulsions having a liquid or semiliquid consistency of the milk type, which are obtained by dispersing a fatty phase in an aqueous phase (O/W) or conversely (W/O), or suspensions or emulsions having a soft consistency of the cream or gel type, or alternatively microcapsules or microparticles, or vesicular dispersions of the ionic and/or nonionic type. It may be optionally applied to the skin in aerosol form. It may also be provided in solid form, for example in the form of a stick. These compositions are prepared according to the customary methods.

This composition may be used as a care product, as a cleansing product or as a makeup product for the skin.

When the composition according to the invention is an emulsion, the proportion of the fatty phase is not limited and may range for example from 5% to 80% by weight, and preferably from 5% to 50% by weight relative to the total weight of the composition. The oils, waxes, emulsifiers and coemulsifiers used in the composition in the form of an emulsion may be chosen from those conventionally used in the cosmetic field. The emulsifier and coemulsifier are preferably present in the composition in a proportion ranging from 0.3% to 30% by weight, and more preferably from 0.5 to 20% by weight relative to the total weight of the composition. The emulsion may additionally contain lipid vesicles.

As oils or waxes which can be used in the invention, there may be mentioned for example mineral oils (liquid paraffin), vegetable oils (liquid fraction of shea butter, sunflower oil), animal oils (perhydrosqualene), synthetic oils (Purcellin oil), silicone oils or waxes (cyclomethicone) and fluorinated oils (perfluoropolyethers), beeswax, carnauba wax or paraffin wax. It is also possible to add to these oils fatty alcohols and fatty acids (stearic acid).

As emulsifiers which can be used in the invention, there may be mentioned for example glyceryl monostearate, polysorbate 60 and polyethylene glycol stearates (20 EO, 40 EO, 100 EO).

In a known manner, the composition of the invention may also contain adjuvants customarily used in the cosmetic and dermatological fields, such as hydrophilic or lipophilic gelling agents, hydrophilic or lipophilic active agents, preservatives, antioxidants, solvents, perfumes, fillers, screening agents, pigments, chelating agents, and colouring matter. The quantities of these various adjuvants are those conventionally used in the fields considered, and are for example from 0.01% to 20% of the total weight of the composition. These adjuvants, depending on their nature, may be introduced into the fatty phase, into the aqueous phase, into the lipid vesicles and/or into the nanoparticles. They should be chosen so as not to damage the desired properties according to the invention.

As hydrophilic gelling agents which can be used in the invention, there may be mentioned carboxyvinyl polymers (carbomer), acrylic copolymers such as acrylate/alkyl acrylate copolymers, polyacrylamides, polysaccharides such as hydroxypropylcellulose, natural gums and clays, and, as lipophilic gelling agents, there may be mentioned modified clays such as bentones, metal salts of fatty acids such as aluminium stearates and hydrophobic silica.

As active agents, it is preferred that the composition according to the invention additionally contain at least one compound chosen from: ascorbic acid and its derivatives such as ascorbyl glucoside, magnesium ascorbyl phosphate and a mixture thereof; niacinamide; tocopherol and its derivatives such as its esters, in particular tocopheryl acetate; galactolipids, extracted in particular from oats.

Other characteristics and advantages of the invention will emerge more clearly from the examples which follow, given by way of illustration and without limitation. In the text which follows, the proportions are given as a percentage by weight, unless otherwise stated.

EXAMPLES

Example 1

Study In Vivo a) Protocol

Two formulas A and B containing caffeine were each applied to a panel of 50 and 62 women, respectively, having stage 2 rosacea (permanent erythema and/or telangiectasia), for two months, at the rate of twice per day. A clinical dermatological evaluation and measurements by Doppler laser and chromametry were performed at the start of the treatment and at the end of eight weeks.

These formulas had the following composition:

| | Formula A | Formula B |
|---|---|---|
| Neutralizer | 0.18% | 0.17% |
| Niacinamide | 4% | 4% |
| Colorants | qs | qs |
| Nonionic surfactant | 3% | 3% |
| Preservatives | qs | qs |
| Alcohol | 5% | 5% |
| Tocopheryl acetate | 0.2% | 0.2% |
| Sodium citrate | 0.3% | 0.3% |
| Caffeine | 0.3% | — |
| Sodium rutinyl disulphate | — | 1% |
| Vitamin K (phytonadione) | — | 0.5% |
| Thickeners | 0.4% | 0.4% |
| Glycerin | 5% | 5% |
| Isononyl isononanoate | 10% | 10% |
| Cetyl alcohol | 1.5% | 1.5% |
| Silicone oil | 5% | 5% |
| Ascorbyl glucoside | 1.5% | 1.5% |
| Fillers | 8% | 8% |
| Glycolipids | 0.25% | 0.25% |
| Citric acid | 0.05% | 0.05% |
| Water | qs 100% | qs 100% | b) Results

At the end of eight weeks of treatment with formula B (comparative example), no significant variation was observed in the parameter "a" (red colour) by chromametry, and a slight decrease was observed in the parameter "L", which indicates darkening of the skin. On the other hand, the reduction in blood flow in the face, measured by Doppler laser, is significant.

By comparison, at the end of eight weeks of treatment with formula A (example according to the invention), a significant reduction was observed in the parameter "a" measured by chromametry, and therefore in the red blotches on the face, and a significant increase was observed in the parameter "L" which indicates a significant lightening of the complexion. The reduction in blood flow in the face is very significant.

c) Conclusion

The above results show that the formula A according to the invention effectively attenuates the red blotches characteristic of the early stages of rosacea, especially as compared to formula B which contains vasculoprotective active agents—which are supposed to be effective against rosacea according to the literature.

Example 2

Cosmetic Compositions

| 2.1 - O/W emulsion | |
|---|---|
| Caffeine | 1% |
| Isononyl isononanoate | 10% |
| Talc | 8% |
| Xanthan gum | 0.2% |
| Alcohol | 5% |
| Glycerin | 5% |
| Mixture of glyceryl stearate and of oxyethylenated stearate (100 EO) | 3% |
| Cetyl alcohol | 1.5% |
| Acrylic copolymer (Pemulen TR2) | 0.3% |
| Sodium hydroxide | 0.2% |
| Preservatives | 1% |
| Water | qs 100 % |
| 2.2 - W/silicones emulsion | |
| Caffeine | 0.1% |
| Apricot oil | 6% |
| Oxyethylenated (18 EO) and oxypropylenated (18 PO) cyclopentasiloxane and polydimethylsiloxane | 15% |
| Glycerin | 23% |
| Fillers | 0.5% |
| Preservatives | 1% |
| Sodium hydroxide | 1.8% |
| Water | qs 100% |

The above written description of the invention provides a manner and process of making and using it such that any person skilled in this art is enabled to make and use the same, this enablement being provided in particular for the subject matter of the appended claims, which make up a part of the original description and including a method for the cosmetic treatment of red skin blotches, comprising the topical application, to the skin, of a composition comprising caffeine in a physiologically acceptable medium.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A method for the treatment of skin redness, comprising: topically applying to the skin of a person suffering from at least one selected from the group consisting of rosacea, erythro-acne rosacea and telangiectasia, a composition comprising: a physiologically acceptable medium, an effective amount of niacinamide and an effective amount of caffeine to treat redness of the skin.

2. The method for the treatment of skin redness, according to claim 1, wherein the skin redness is due to rosacea.

3. The method for the treatment of skin redness, according to claim 1, wherein the composition comprises 0.1-1% by weight of caffeine, relative to the total weight of the composition.

4. The method for the treatment of skin redness, according to claim 1, wherein the composition further comprises at least one compound selected from the group consisting of ascorbic acid and its derivatives; and tocopherol and its derivatives.

5. The method for the treatment of skin redness, according to claim 4, wherein the composition further comprises at least one ascorbic acid derivative selected from the group consisting of ascorbyl glucoside and magnesium ascorbyl phosphate.

6. The method for the treatment of skin redness, according to claim 4, wherein the composition further comprises at least one tocopherol derivative selected from the group consisting of tocopherol esters.

7. The method for the treatment of skin redness, according to claim 1, wherein the composition is applied to the skin of the face of the person in need thereof.

8. The method for the treatment of skin redness, according to claim 1, wherein the composition comprises 0.05%-3% by weight of caffeine, relative to the total weight of the composition.

9. The method for the treatment of skin redness, according to claim 6, wherein the composition further comprises tocopheryl acetate.

10. The method for the treatment of skin redness, according to claim 1, wherein the composition is applied to the skin of a person in need thereof having rosacea.

11. The method for the treatment of skin redness, according to claim 3, wherein the composition is applied to the skin of a person in need thereof having rosacea.

12. The method for the treatment of skin redness, according to claim 8, wherein the composition is applied to the skin of a person in need thereof having rosacea.

13. The method for the treatment of skin redness, according to claim 1, wherein the composition is applied to the skin of a person in need thereof having erythro-acne rosacea.

14. The method for the treatment of skin redness, according to claim 3, wherein the composition is applied to the skin of a person in need thereof having erythro-acne rosacea.

15. The method for the treatment of skin redness, according to claim 8, wherein the composition is applied to the skin of a person in need thereof having erythro-acne rosacea.

16. The method for the treatment of skin redness, according to claim 9, wherein the composition is applied to the skin of a person in need thereof having at least one of erythro-acne rosacea, and telangiectasia, and wherein the composition comprises 0.1-1% by weight of caffeine, relative to the total weight of the composition.

* * * * *